(12) United States Patent
Honda

(10) Patent No.: US 6,853,949 B2
(45) Date of Patent: Feb. 8, 2005

(54) LIVING BODY DATA MANAGEMENT SYSTEM WITH FUNCTION OF DISPLAYING GROWTH PROCESS GRAPH

(75) Inventor: Yuka Honda, Tokyo (JP)

(73) Assignee: Tanita Corporation, Tokyo (JP)

( * ) Notice: Subject to any disclaimer, the term of this patent is extended or adjusted under 35 U.S.C. 154(b) by 115 days.

(21) Appl. No.: 10/226,203

(22) Filed: Aug. 23, 2002

(65) Prior Publication Data

US 2003/0046009 A1 Mar. 6, 2003

(30) Foreign Application Priority Data

Aug. 29, 2001 (JP) .................................... 2001-259014

(51) Int. Cl.$^7$ .......................... G01G 19/00; G06F 15/00
(52) U.S. Cl. .................. 702/173; 702/127; 702/176; 177/5; 177/25.19
(58) Field of Search ................... 702/179, 180, 702/182

(56) References Cited

U.S. PATENT DOCUMENTS 4,113,039 A * 9/1978 Ozaki et al. ............. 177/25.19
4,301,879 A * 11/1981 Dubow ........................ 177/5
6,321,112 B1 * 11/2001 Masuo ....................... 600/547

FOREIGN PATENT DOCUMENTS

| EP | 1076230 | 4/2001 |
| EP | 1219937 | 7/2002 |
| JP | 9-21689 | 1/1997 |
| JP | 9-238926 | 9/1997 |

* cited by examiner

Primary Examiner—Bryan Bui
(74) Attorney, Agent, or Firm—McDermott Will & Emery LLP

(57) ABSTRACT

A living body data management system graphically displays reference growth range data obtained as average growth ranges of body weights and heights of infants during a period spanning from birth to under the age of seven, based on body weight data and height data collected from a number of infants. The system displays the reference data as growth curve graphs (H, W) on a graph display means, and further displays a subject's acquired data over the growth curve graphs (H, W), thereby enabling a user to visually comprehend the growth status represented by the acquired data by contrasting the acquired data with the growth curve graphs (H, W) at a glance.

3 Claims, 5 Drawing Sheets

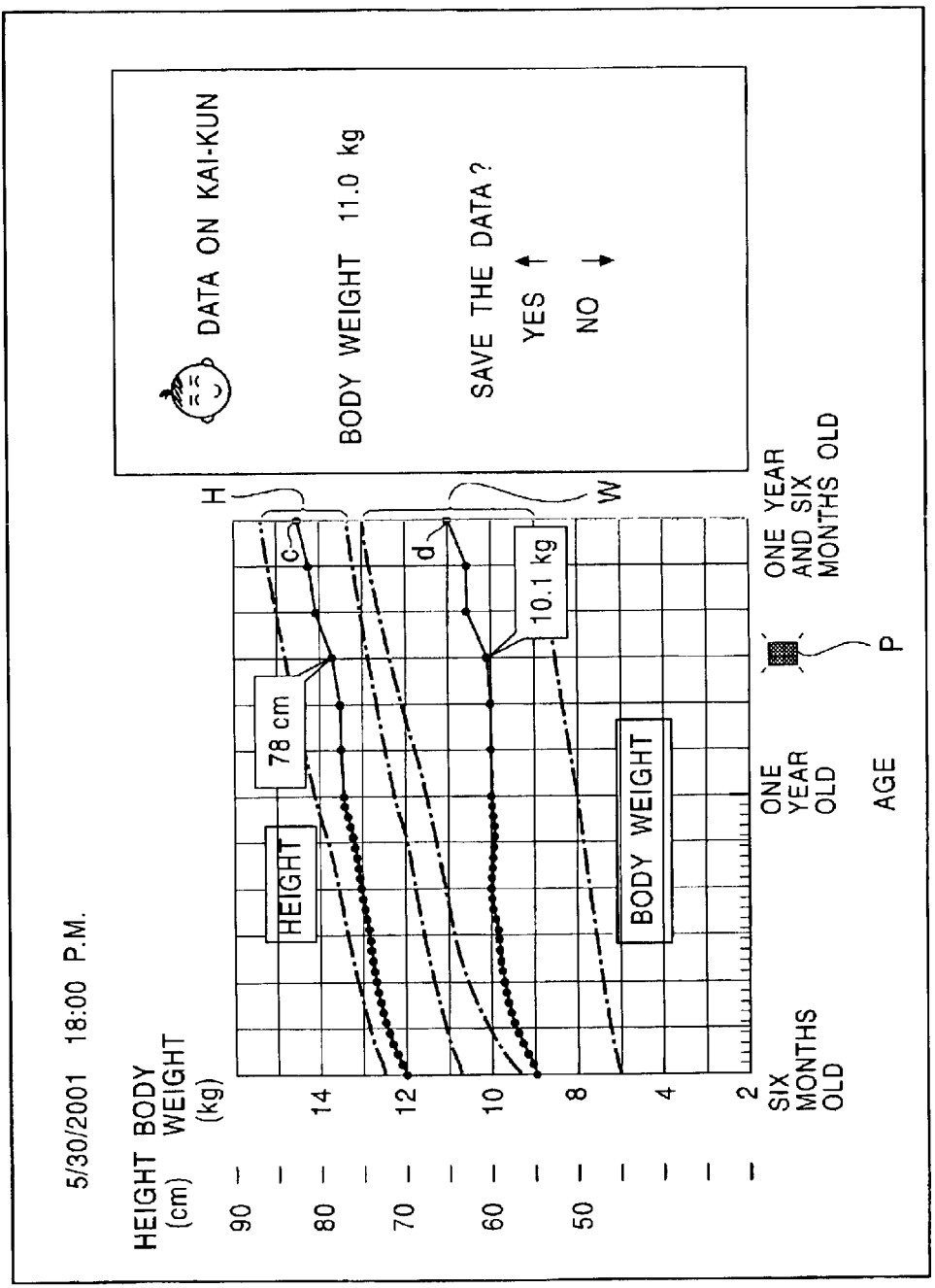

LIVING BODY DATA MANAGEMENT SYSTEM WITH FUNCTION OF DISPLAYING GROWTH PROCESS GRAPH

BACKGROUND OF THE INVENTION (i) Field of the Invention

The present invention relates to a living body data management system with a function of displaying a growth process graph which allows an examiner to realize growth trends of a body weight and height of a subject who is in a process of growing in contrast to reference growth trends of a body weight and height.

(ii) Description of the Related Art

It has heretofore been proposed to administrate a dietary life or health of a subject based on a trend in changes in a bodyweight of the subject by use of, for example, a system (refer to Japanese Patent Application Laid-Open No. 21689/1997) which displays body weights of the subject which are stored in body weight storing means in chronological order on display means as a graph.

However, the above system is not capable of allowing an examiner to realize the graphed trend in changes in the body weight of the subject in visual contrast to a reference trend in changes in a body weight. Meanwhile, in view of the fact that those who are fat in childhood often become fat when they enter adulthood, it has been becoming increasingly important to administrate trends in changes in a height and body weight in a stage in a process when growths of the height and body weight are significant.

Under the above circumstances, an object of the present invention is to provide a living body data management system with a function of displaying a growth process graph which allows an examiner to visually realize growth trends of a height and body weight of a subject who is in a process in which growths of the height and body weight are significant in contrast to reference growth trends of a height and body weight.

SUMMARY OF THE INVENTION

It is a primary object of the present invention to provide a living body data management system with a function of displaying a growth process graph.

It is a still further object of the present invention to provide a living body data management system with a function of displaying a growth process graph, which comprises body weight data acquiring means, acquired data storing means, reference growth range data storing means and graph display means, wherein the body weight data acquiring means acquires body weight data of a subject who is in a process of growing, the acquired data storing means continuously stores the body weight data acquired by the body weight data acquiring means as acquired data, the reference growth range data storing means stores reference growth range data determined as a reference growth range of a body weight during a period in the growth process, and the graph display means displays graphs showing a correlation between the reference growth range data stored in the reference growth range data storing means and the acquired data stored in the acquired data storing means.

It is a still further object of the present invention to provide a living body data management system with a function of displaying a growth process graph, which comprises height data acquiring means, acquired data storing means, reference growth range data storing means and graph display means, wherein the height data acquiring means acquires height data of a subject who is in a process of growing, the acquired data storing means continuously stores the height data acquired by the height data acquiring means as acquired data, the reference growth range data storing means stores reference growth range data determined as a reference growth range of a height during a period in the growth process, and the graph display means displays graphs showing a correlation between the reference growth range data stored in the reference growth range data storing means and the acquired data stored in the acquired data storing means.

It is a still further object of the present invention to provide a living body data management system with a function of displaying a growth process graph, which comprises body weight data acquiring means, height data acquiring means, acquired data storing means, reference growth range data storing means and graph display means, wherein the body weight data acquiring means acquires body weight data of a subject who is in a process of growing, the height data acquiring means acquires height data of the subject who is in a process of growing, the acquired data storing means continuously stores the body weight data acquired by the body weight data acquiring means and the height data acquired by the height data acquiring means as acquired data, the reference growth range data storing means stores reference growth range data determined as reference growth ranges of a body weight and height during a period in the growth process, and the graph display means displays graphs showing correlations between the reference growth range data stored in the reference growth range data storing means and the acquired data stored in the acquired data storing means.

According to these systems, graphs showing correlation(s) between the reference growth range data stored in the reference growth range data storing means and the acquired data stored in the acquired data storing means are displayed on the graph display means. Thereby, an examiner can realize growth status(es) of the acquired data in contrast to the reference growth range data at a glance.

Further, the living body data management system of the present invention further comprises acquisition time point specifying means for specifying a time point at which the acquired data has been acquired, and the acquired data storing means continuously stores the acquired data if the acquisition time point of the acquired data which has been specified by the acquisition time point specifying means matches a growth administration time point. According to the system, only acquired data whose acquisition time point matches a growth administration time point is stored in the acquired data storing means. Thereby, a large amount of acquired data can be stored.

Further, the period in the growth process to which the reference growth range data stored in the reference growth range data storing means belongs is a period spanning from birth until the subject reaches under the age of seven. Thereby, an examiner can visually realize a growth status of the subject in an early stage of growth by contrasting the acquired data with the reference growth range data at a glance.

Further, the period in the growth process to which the reference growth range data stored in the reference growth range data storing means belongs is a period spanning from birth until the subject reaches the age of one. Thereby, an examiner can visually realize a growth status of the subject particularly in infancy in which growths of a body weight and height are significant, by contrasting the acquired data with the reference growth range data at a glance.

Further, the growth administration time point is set on a weekly basis during a period spanning from birth until the subject reaches the age of one and set on a monthly basis after the subject reaches the age of one. When intervals between growth administration time points are set to be short only during infancy which is a period between birth and the age of one, a large amount of acquired data can be stored, and a growth status of the subject particularly in the infancy in which growths of a body weight and height are significant can be realized clearly in an early stage.

Further, the graph display means displays graphs which are scrollable in directions of a vertical axis which represents acquired data and a horizontal axis which represents a period spanning from birth to a current age of the subject. Thereby, since the graphs are scrollable in directions of the vertical and horizontal axes, an examiner can view the graphs covering a whole period for administrating growth in a right size even if a display screen of the graph display means is small.

Further, the graph display means displays acquired data corresponding to a specified growth administration time point. Thereby, since acquired data corresponding to a specified growth administration time point is displayed, an examiner can realize acquired data corresponding to a growth administration time point which is associated with the acquired data that the examiner wants to know, without reading a scale.

BRIEF DESCRIPTION OF THE DRAWINGS

FIG. 5 is another example of data displayed on the living body data management system according to the present invention.

Figure 1:
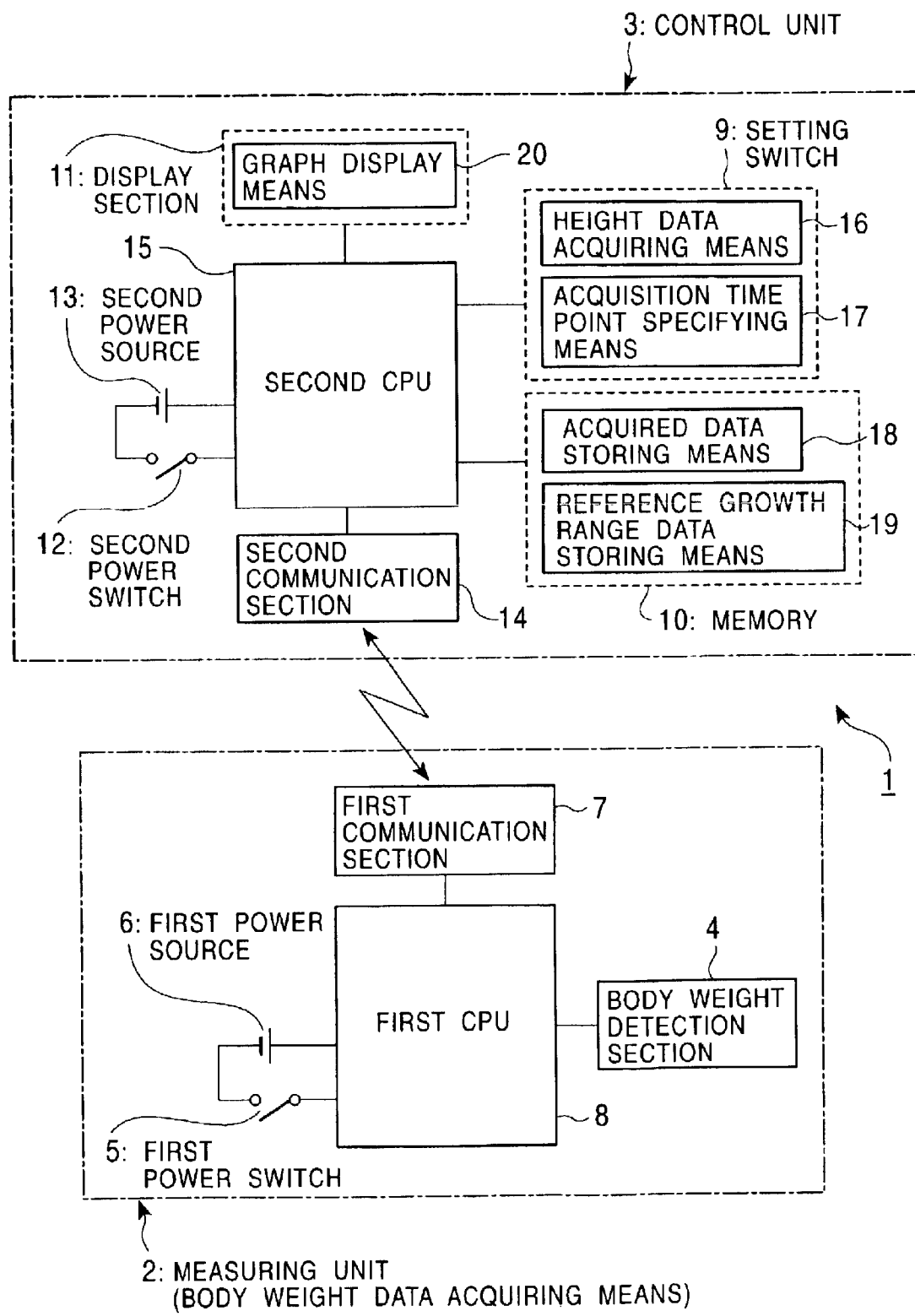
FIG. 1 is a block diagram showing a constitution of a living body data management system with a function of displaying a growth process graph according to the present invention.

Reference numeral 1 denotes a living body data management system with a function of displaying a growth process graph; 2 a measuring unit (body weight data acquiring means); 3 a control unit; 4 a body weight detection section; 5 a first power switch; 6 a first power source; 7 a first communication section; 8 a first CPU; 9 a setting switch; 10 a memory; 11 a display section; 12 a second power switch; 13 a second power source; 14 a second communication section; 15 a second CPU; 16 height data acquiring means; 17 acquisition time point specifying means; 18 acquired data storing means; 19 reference growth range data storing means; 20 graph display means; a and d newly acquired body weight data; b and c newly acquired height data; H a growth curve graph of a height; W a growth curve graph of a body weight; and P a cursor.

DETAILED DESCRIPTION OF THE PREFERRED EMBODIMENT

Hereinafter, an embodiment of the present invention will be described with reference to the drawings.

Figure 2:
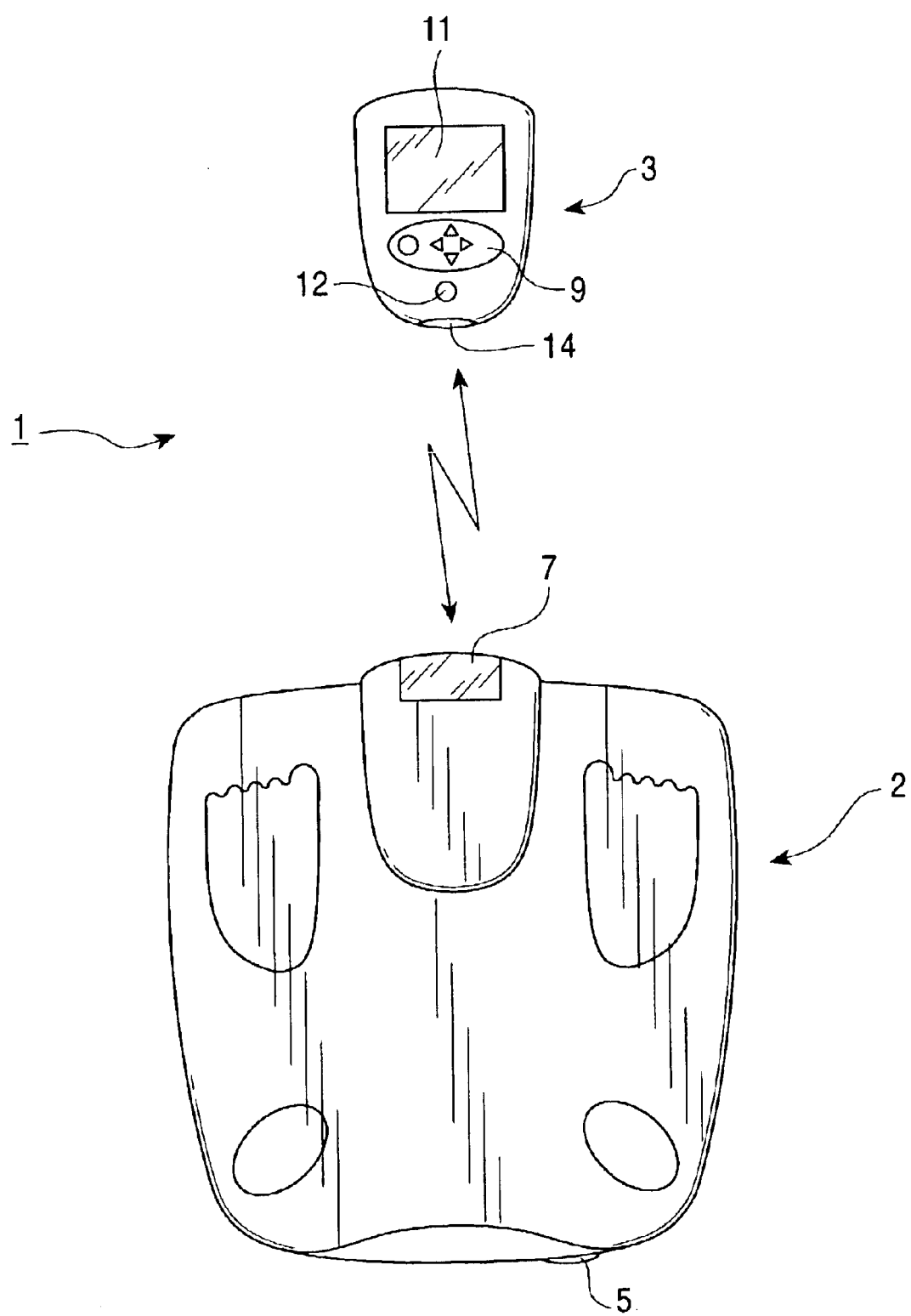
FIG. 2 is a plan view of an external appearance of the living body data management system according to the present invention.

Firstly, a constitution of a living body data management system with a function of displaying a growth process graph is shown in a block diagram in FIG. 1. Further, a plan view of its external appearance is shown in FIG. 2. A living body data management system 1 with a function of displaying a growth process graph according to the present invention is roughly constituted by a measuring unit 2 and a control unit 3.

The measuring unit 2 is body weight data acquiring means for acquiring body weight data of a subject. It comprises a body weight detection section 4 for detecting body weight data, a first power switch 5 for turning on the measuring unit 2, a first power source 6 for supplying power to the measuring unit 2 according to opening and closing of the first power switch 5, a first communication section 7 for carrying out data communication with a second communication section 14 of the control unit 3, and a first CPU 8 for controlling operations of these sections and performing computations.

The control unit 3 comprises a setting switch 9, a memory 10, a display section 11, a second power switch 12 for turning on the control unit 3, a second power source 13 for supplying power to the control unit 3 according to opening and closing of the second power switch 12, the second communication section 14 for carrying out data communication with the first communication section 7 of the measuring unit 2, and a second CPU 15 for controlling operations of these sections and performing computations.

The setting switch 9 of the control unit 3 is used to enter and set personal data of a subject such as a name, date of birth and gender and to operate a graph displayed on the display section 11. Further, the setting switch 9 is also height data acquiring means 16 for acquiring height data of a subject. The means 16 acquires height data of a subject by causing the subject to enter and set the height data of the subject by means of the setting switch 9. In addition, the setting switch 9 is also acquisition time point specifying means 17 for specifying a time point at which body weight data and height data have been acquired as acquired data. The means 17 specifies a time point at which body weight data and height data have been acquired by causing a subject to enter and set a date and time of measurements by means of the setting switch 9.

Further, the memory 10 comprises acquired data storing means 18 and reference growth range data storing means 19. The acquired data storing means 18 continuously store, as acquired data, body weight data acquired by the body weight acquiring means, i.e., body weight data sent from the measuring unit 2, and height data acquired by the height data acquiring means 16, i.e., height data entered and set by means of the setting switch 9. The reference growth range data storing means 19 stores in advance reference growth range data obtained as average growth ranges of body weights and heights of infants during a period spanning from birth until they reach under the age of seven, based on body weight data and height data collected from a number of infants during a period spanning from birth until they reach under the age of seven.

Further, the display section 11 displays personal data and height data of a subject which have been entered and set by means of the setting switch 9 and body weight data sent from the measuring unit 2. In addition, the display section 11 is also graph display means 20 for displaying graphs showing correlations between reference growth range data stored in the reference growth range data storing means 19 and acquired data stored in the acquired data storing means 18.

Figure 3:
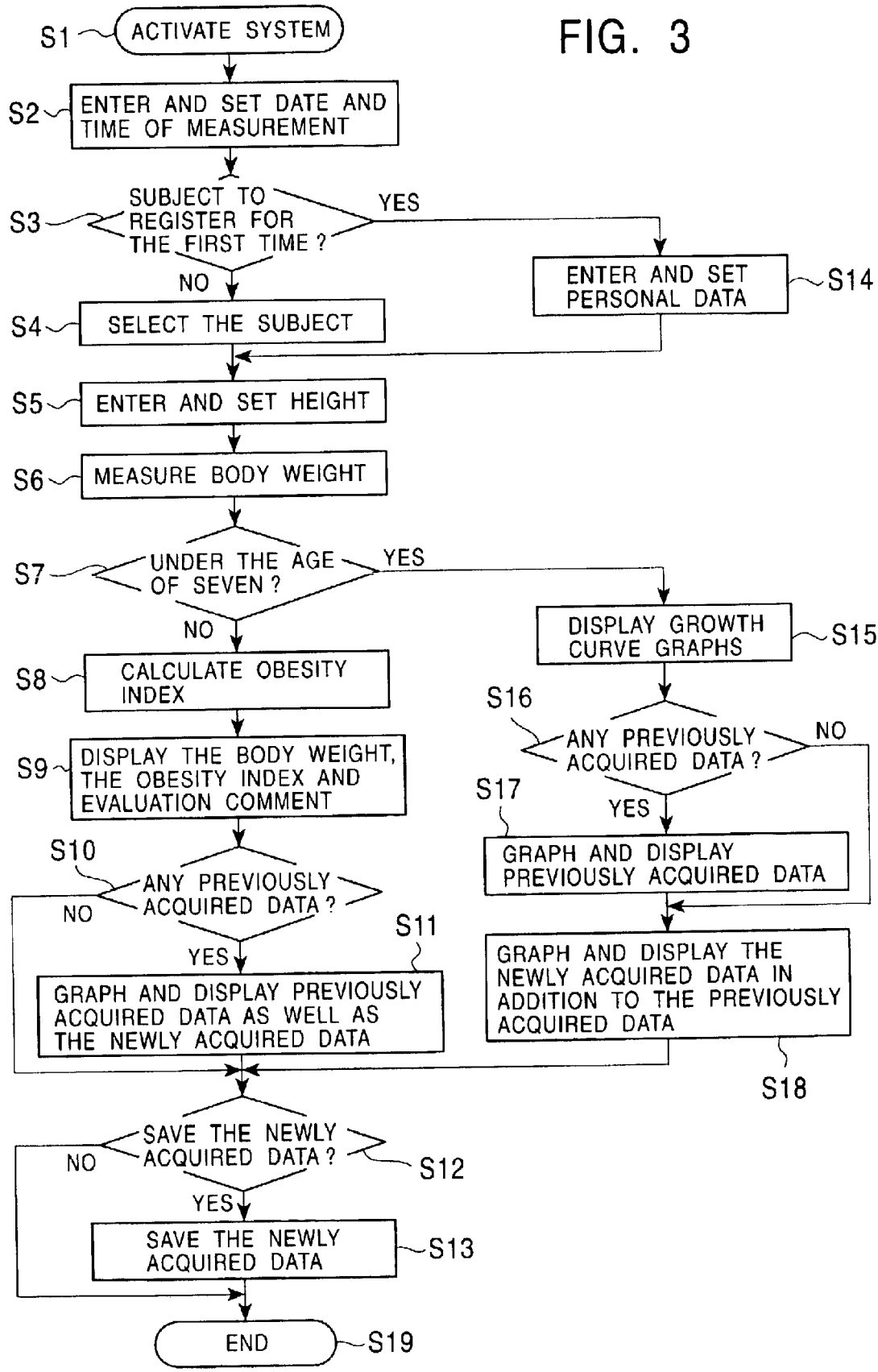
FIG. 3 is a flowchart illustrating steps performed by the living body data management system according to the present invention.

Next, operations of the present invention will be described with reference to a flowchart in FIG. 3 which shows steps performed by the living body data management system with a function of displaying a growth process graph according to the present invention. The operations of the present invention will be described without describing operations of the measuring unit 2 separately from those of the control unit 3. Firstly, the living body data management system 1 with a function of displaying a growth process graph according to the present invention is activated by closing the first power switch 5 of the measuring unit 2 and the second power switch 12 of the control unit 3 (STEP 1).

Then, a screen for entering and setting a date and time of measurement is displayed on the display section 11. A subject enters and sets a date and time of measurement by means of the setting switch 9 as the acquisition time point specifying means 17 (STEP 2).

Then, a screen which asks whether the subject is one who is to register for the first time ("YES") or not ("NO") is displayed on the display section 11 (STEP 3). If the subject has never registered, the subject chooses "YES" in STEP 3 and then enters and sets personal data of the subject such as a name, date of birth and gender in accordance with a screen displayed on the display section 11 (STEP 14).

Meanwhile, if the subject has registered before, the subject chooses "NO" in STEP 3. Thereby, a screen for selecting a subject (for example, a screen showing a list of subjects who have registered in the past) is displayed on the display section 11, and the subject finds and selects himself/herself on the screen (STEP 4).

Then, a screen for entering and setting a height of the subject is displayed on the display section 11. The subject enters and sets height data at the time of measurement of the subject by means of the setting switch 9 as the height data acquiring means 16 (STEP 5). The height data entered and set by means of the setting switch 9 is stored in the acquired data storing means 18 temporarily.

Then, a screen for encouraging the subject to measure his/her body weight is displayed on the display section 11. Then, body weight data of the subject is measured by the measuring unit 2 which is the body weight data acquiring means (STEP 6).

Then, after the body weight is measured by the measuring unit 2, the body weight data is stored in the acquired data storing means 18 temporarily. Subsequently, the second CPU 15 calculates age of the subject from the date of measurement entered and set in STEP 2 and the date of birth entered in STEP 14 so as to determine whether the subject is under the age of seven (STEP 7). At this point, when the subject is one year old or younger, the age of the subject is determined in months and weeks, while when the subject is over one year old, the age of the subject is determined in years and months.

When the subject is not under the age of seven ("NO" in STEP 7), an obesity index (%) of the subject is calculated (STEP 8). An obesity index (%) is determined based on a formula: (measured body weight (kg)−height$^2$ (m)×22)÷(height$^2$ (m)×22)×100.

Figure 4:
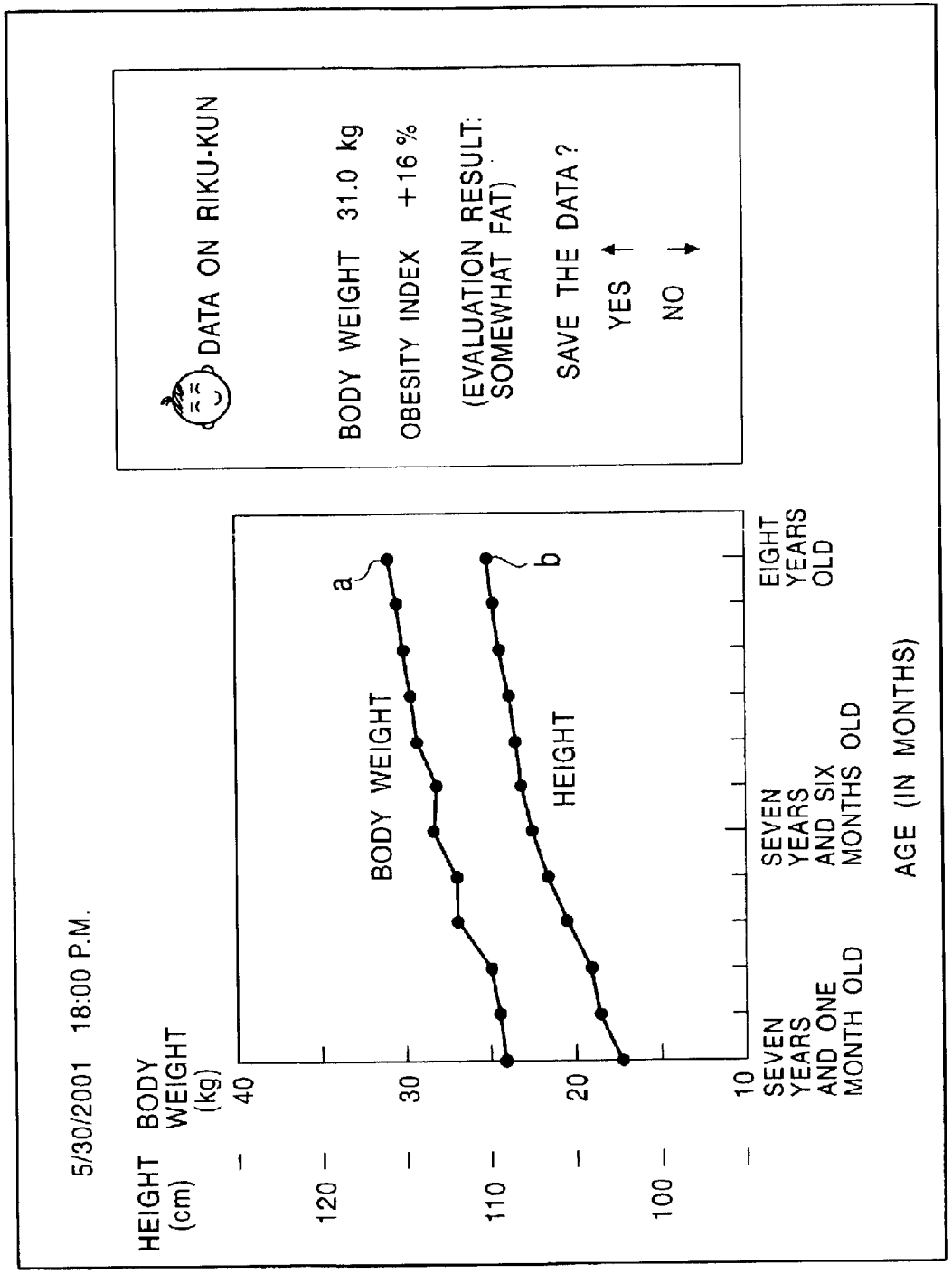
FIG. 4 is an example of data displayed on the living body data management system according to the present invention.

Then, on the display section 11, as shown in FIG. 4, the obesity index (%) calculated by the second CPU 15, a comment on the obesity index, a symbol characterizing the subject, and the name (Riku-kun) of the subject are displayed (STEP 9). As the comment, "somewhat fat" is displayed when the obesity index is 15% or higher and lower than 20%, "fat" is displayed when the obesity index is 20% or higher and lower than 30%, "too fat" is displayed when the obesity index is 30% or higher, and "thin" is displayed when the obesity index is −15% or lower.

Then, the second CPU 15 determines whether there are any previously acquired data in the acquired data storing means 18 (STEP 10). When there are previously acquired data ("YES" in STEP 10), the previously acquired data as well as the newly acquired data (body weight data a and height data b obtained in the latest measurements) are displayed on the display section 11 as a graph as shown in FIG. 4 (STEP 11).

Meanwhile, when the subject is under the age of seven ("YES" in STEP 7), growth curve graphs obtained by graphing reference growth range data stored in the reference growth range data storing means 19 in advance are displayed on the display section 11 (STEP 15). The growth curve graphs displayed on the display section 11, as shown in FIG. 5, are displayed as average growth ranges (a growth curve graph of a body weight is a range W, and a growth curve graph of a height is a range H) of a body weight and height from birth to a current age of the subject, on a screen with a vertical axis representing a body weight and a height and a horizontal axis representing a period between birth and the current age of the subject. Together with the growth curve graphs, the newly acquired data, a symbol characterizing the subject, and the name (Kai-kun) of the subject are also displayed on the display section 11.

Then, the second CPU 15 determines whether there are any previously acquired data which are continuously stored in the acquired data storing means 18 (STEP 16). When there are previously acquired data ("YES" in STEP 16), the previously acquired data which are continuously stored in the acquired data storing means 18 are displayed over the growth curve graphs displayed on the display section 11 as shown in FIG. 5 (STEP 17). Thus, the graphs displayed on the display section 11 represent correlations between the reference growth range data stored in the reference growth range data storing means 19 in advance and the previously acquired data stored in the acquired data storing means 18.

Meanwhile, when it has been determined in STEP 16 that there are no previously acquired data ("NO" in STEP 16), only the newly acquired data which have been temporarily stored in the acquired data storing means 18 are displayed over the growth curve graphs displayed on the display section 11. Further, after STEP 17, as shown in FIG. 5, the newly acquired data (body weight data d and height data c obtained in the latest measurements) are also displayed in addition to the previously acquired data displayed in STEP 17 (STEP 18).

Then, after STEP 11 or STEP 18, when a cursor P as shown in FIG. 5 which appears on the horizontal axis representing a period between birth and the current age of the subject is moved in a horizontal direction by means of the setting switch 9, a screen of the display section 11 which displays the graphs is scrolled not only in a horizontal direction according to the movement of the cursor P but also in a vertical direction so as to cause graph portions of body weights and heights which correspond to a position of the horizontally moved cursor P to fit in the screen. Further, as shown in FIG. 5, body weight data (10.1 kg) and height data (78 cm) at points on the graphs which correspond to a point on the horizontal axis where the cursor P appears are displayed near the points on the corresponding graphs, pointing at the points on the graphs.

Meanwhile, when there are no previously acquired data in the acquired data storing means 18 ("NO" in STEP 10), it is determined after STEP 11 or STEP 18 whether the acquisition time point of the newly acquired data stored in the acquired data storing means 18 falls on a growth administration time point (STEP 12). To be more specific, it is determined whether the acquisition time point of the newly acquired data which has been specified by the acquisition time point specifying means 17 matches a growth administration time point which is set on a weekly basis after birth when the subject is one year old or younger or on a monthly basis after birth when the subject is over one year old.

Then, when the acquisition time point of the newly acquired data, in other words, the age determined in STEP 7, matches a growth administration time point ("YES" in STEP 12), the newly acquired data is stored in the acquired data storing means 18 subsequently to previously acquired data (STEP 13).

Meanwhile, when the acquisition time point of the newly acquired data does not match any growth administration time point ("NO" in STEP 12) or after STEP 13, the system 1 ends the whole procedure (STEP 19).

As described above, the living body data management system 1 with a function of displaying a growth process graph displays, as the growth curve graphs (H, W), the reference growth range data obtained as average growth ranges of body weights and heights of infants during a period spanning from birth until they reach under the age of seven based on bodyweight data and height data collected from a number of infants during a period spanning from birth until they reach under the age of seven, on the display section 11 which is the graph display means 20 and further displays the acquired data stored in the acquired data storing means 18 over the growth curve graphs (H, W) displayed on the display section 11. Thereby, an examiner can realize growth statuses of the acquired data by contrasting the acquired data with the growth curve graphs (H, W) at a glance. In particular, since the reference growth range data are obtained as average growth ranges of body weights and heights of infants during a period spanning from birth until they reach under the age of seven, an examiner can realize the growth statuses of the acquired data in an early stage of growth.

Further, when the acquisition time point of the newly acquired data which has been determined from the date and time of measurements entered and set by means of the setting switch 9 as the acquisition time point specifying means 17 matches a growth administration time point which indicates how many weeks have just passed since birth when the subject is one year old or younger or indicates how many months have just passed since birth when the subject is over one year old, the newly acquired data is stored in the acquired data storing means 18 continuously. Thus, by setting intervals between growth administration time points to be short only during infancy which is a period between birth and the age of one, a large amount of acquired data can be stored, and a growth status of the subject particularly in the infancy in which growths of a body weight and height are significant can be realized clearly in an early stage.

Further, along with horizontal movement of the cursor P which appears on the horizontal axis representing a period between birth and the current age of the subject by means of the setting switch 9, the graph displaying screen of the display section 11 as the graph display means 20 is scrolled not only in a horizontal direction according to the movement of the cursor P but also in a vertical direction so as to cause graph portions of body weights and heights which correspond to a position of the horizontally moved cursor P to fit in the screen. Thereby, an examiner can view the graphs covering a whole period for administrating growth in a right size even if the screen for displaying the graphs is small.

Further, when the cursor P is moved, i.e., when a growth administration time point is specified, body weight data and height data at points on the graphs which correspond to a position of the cursor P, i.e., acquired data corresponding to the specified growth administration time point, are displayed near the points on the corresponding graphs, pointing at the points on the graphs. Thereby, an examiner can realize acquired data corresponding to a growth administration time point which is associated with the acquired data that the examiner wants to know, without reading a scale.

Further, in the above embodiment, although the reference growth range data are average growth ranges of body weights and heights of infants during a period spanning from birth until they reach under the age of seven, the reference growth range data may be average growth ranges of body weights and heights of infants during a period spanning from birth until they reach the age of one. Thereby, an examiner can realize a growth status of the subject particularly in an early stage, i.e., in infancy in which growths of a body weight and height are significant, by contrasting the acquired data with the reference growth range data at a glance.

Further, in the above embodiment, body weight data is acquired by measuring a body weight by means of the measuring unit 2, and height data is acquired by entering and setting a height by means of the setting switch 9. However, the body weight data may be acquired by entering and setting the body weight by means of the setting switch 9, and the height data may be acquired by measuring the height by means of the measuring unit 2. Alternatively, both the body weight data and the height data may be acquired by means of only the measuring unit 2 or only the setting switch 9. In addition, only either one of the body weight data and the height data may be involved.

Further, in the above embodiment, the reference growth range data stored in the reference growth range data storing means 19 in advance are average growth ranges of body weights and heights of infants during a period spanning from birth until they reach under the age of seven based on body weight data and height data collected from a number of infants during a period spanning from birth until they reach under the age of seven. However, the reference growth range data may also be reference growth range data obtained as average growth ranges of body weights and heights of infants during a period with a low disease rate or other periods in a growth process.

Further, in the above embodiment, acquired data corresponding to time points specified by the acquisition time point specifying means 17 are stored continuously in the acquired data storing means 18. However, it is also possible that all data acquired by each measurement are stored in the acquired data storing means 18 and displayed as graphs on the graph display means 20 with a horizontal axis representing the number of measurements after birth by limiting intervals between the measurements.

Further, in the above embodiment, a growth administration time point is set on a weekly basis when a subject is one year old or younger or on a monthly basis when the subject is over one year old. However, the growth administration time point may be set on a biweekly basis when the subject is one year old or younger or on a bimonthly basis when the subject is over one year old. Alternatively, the growth administration time point may be set on a daily basis when the subject is one year old or younger or on a weekly basis or at other intervals when the subject is over one year old. Further, a selecting switch may be provided to switch between two different measurement modes, e.g., a weekly basis when the subject is one year old or younger and a monthly basis when the subject is over one year old, according the age of the subject.

As described above, the living body data management system with a function of displaying a growth process graph according to the present invention displays graphs showing correlations between reference growth range data and acquired data on the graph display means. Thereby, an examiner can visually realize growth statuses of the acquired data by contrasting the acquired data with the reference growth range data at a glance.

Further, since only acquired data corresponding to growth administration time points are stored in the acquired data storing means, a large amount of acquired data can be stored.

Further, the reference growth range data covers a period spanning from birth until a subject reaches under the age of seven in a growth process. Thereby, an examiner can visually realize a growth status of the subject in an early stage of growth by contrasting acquired data with the reference growth range data at a glance.

Alternatively, the reference growth range data may cover a period spanning from birth until the subject reaches the age of one in a growth process. Thereby, an examiner can visually realize a growth status of the subject particularly in infancy in which growths of a body weight and height are significant, by contrasting acquired data with the reference growth range data at a glance.

Further, only during infancy which is a period between birth and the age of one, acquired data are stored continuously in the acquired data storing means at short intervals between growth administration time points. Thereby, a large amount of acquired data can be stored, and a growth status of the subject particularly in the infancy in which growths of a body weight and height are significant can be realized clearly in an early stage.

Further, the graph display means displays graphs which are scrollable in directions of vertical and horizontal axes. Thereby, an examiner can view the graphs covering a whole period for administrating growth in a right size even if a display screen of the graph display means is small.

Further, the graph display means displays acquired data corresponding to a specified growth administration time point. Thereby, an examiner can realize acquired data corresponding to a growth administration time point which is associated with the acquired data that the examiner wants to know, without reading a scale.

What is claimed is:

1. A living body data management system with a function of displaying a growth process graphs, comprising:

body weight data acquiring means, height data acquiring means, a setting switch, acquisition time point specifying means, acquired data storing means, reference growth range data storing means, and graph display means, wherein the body weight data acquiring means acquires body weight data of a subject who is in a process of growing, wherein the height data acquiring means acquires height data of the subject who is in a process of growing, wherein the setting switch is for entering and setting gender as personal data of the subject, wherein the acquisition time point specifying means specify a time point at which the body weight data acquired by the body weight data acquiring means and the height data acquired by the height data acquiring means have been acquired as acquired data, wherein the acquired data storing means continuously stores the acquired data if the acquisition time point of the acquired data which has been specified by the acquisition time point specifying means matches a growth administration time point, the growth administration time point being set on a weekly basis during a period spanning from birth until the subject reaches the age of one and set on a monthly basis after the subject reaches the age of one, wherein the reference growth range data storing means stores reference growth range data determined as reference growth ranges of a body weight and height during a period in the growth process, and wherein the graph display means displays graphs showing correlations between the reference growth range data stored in the reference growth range data storing means and the acquired data stored in the acquired data storing means.

2. The system of claim 1, wherein the graph display means displays graphs which are scrollable in directions of a vertical axis which represents acquired data and a horizontal axis which represents a period spanning from birth to a current age of the subject.

3. The system of claim 1, wherein the graph display means displays acquired data corresponding to a specified growth administration time point.

* * * * *